United States Patent

Callen et al.

[11] Patent Number: 5,098,668
[45] Date of Patent: Mar. 24, 1992

[54] HF ALKYLATION UNIT WITH ACID EVACUATION SYSTEM

[75] Inventors: Robert B. Callen, McLean, Va.; Saverio G. Greco, Princeton Junction, N.J.; Ronald D. McGihon, Chantilly, Va.; Zay K. Risinger, Pennington, N.J.; Paul W. Snyder, Washington Crossing, Pa.

[73] Assignee: Mobil Oil Corporation, Fairfax, Va.

[21] Appl. No.: 489,648

[22] Filed: Mar. 7, 1990

[51] Int. Cl.⁵ .......................... G05D 7/00; B01J 10/00
[52] U.S. Cl. .................................. 422/111; 422/189; 422/188
[58] Field of Search ............... 422/189, 111, 188, 187, 422/129, 215, 62; 585/714, 715, 716, 723

[56] References Cited

U.S. PATENT DOCUMENTS

| | | | |
|---|---|---|---|
| 2,437,544 | 3/1948 | Marisic | 585/715 |
| 2,850,552 | 9/1958 | Ogle | 585/723 |
| 2,894,999 | 7/1959 | Lawson | 585/715 |
| 3,206,524 | 9/1965 | Plaster | 585/716 |
| 3,716,343 | 11/1973 | Chapman | 422/215 |
| 4,579,998 | 4/1986 | Hutson | 585/716 |

Primary Examiner—Douglas W. Robinson
Assistant Examiner—Timothy J. Reardon
Attorney, Agent, or Firm—Alexander J. McKillop; Charles J. Speciale; Malcolm D. Keen

[57] ABSTRACT

An HF alkylation unit with improved safety features including an acid storage and evacuation receiver which maintains a large proportion of the acid inventory of the unit at a remote, safe location. The unit also has an acid evacuation system which is capable of transferring the acid from the reactor section of the unit to the receiver within a very short period of time in the event of an uncontrolled release from the unit. The acid receiving drum is connected to the remainder of the unit by means of acid transfer lines for rapidly evacuating the acid and is desirably maintained at a pressure lower than the reactor section of the unit to enable the acid to be pressured into the receiver. The pressure in the receiver is suitably maintained by a pressure balancing line to the fractionation system at a lower pressure than the alkylation reaction itself. Unit acid inventory may be reduced by the use of an acid settler provided with an acid boot and coalescing baffles which promote a phase separation.

11 Claims, 4 Drawing Sheets

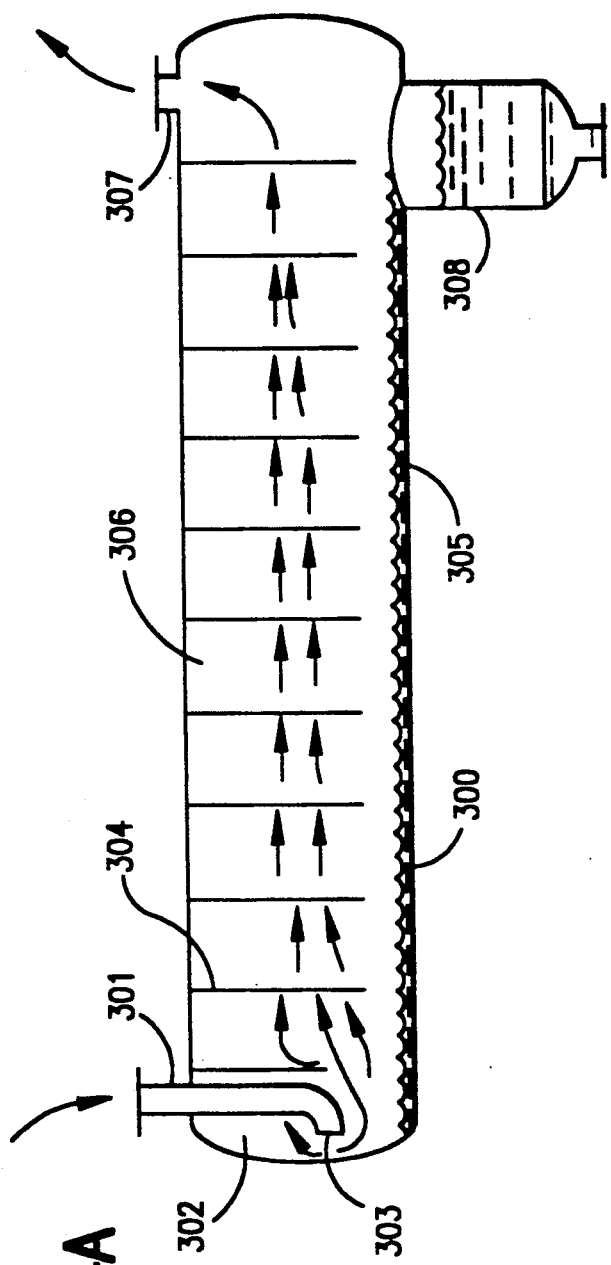
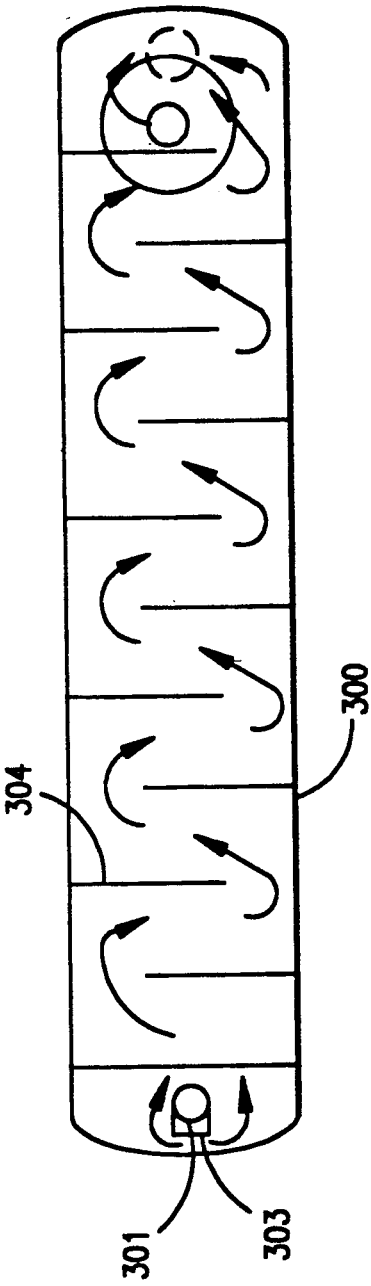

HF ALKYLATION UNIT WITH ACID EVACUATION SYSTEM

FIELD OF THE INVENTION

The invention relates to an alkylation process using hydrofluoric acid (HF) as the alkylation catalyst. In particular, it relates to HF alkylation units with improved safety features and, in one embodiment, to an HF alkylation unit employing a reduced inventory of HF alkylation catalyst.

BACKGROUND OF THE INVENTION

HF alkylation is an established process in the petroleum refining industry which is used on a wide scale for the production of high quality, high octane gasoline from lower boiling feeds. Commercial refinery plants usually operate with an isoparaffin stream, predominantly isobutane, which is alkylated with $C_3$ to $C_4$ olefins to form branched chain paraffin products boiling in the gasoline range, typically up to about 385° F. (about 197° C.). A major source of the olefin chargestock is the light olefin fraction from fluid catalytic cracking (FCC units), comprising principally $C_3$–$C_4$ olefins; the olefins in this fraction, especially the isobutene, readily alkylate iso-butane in the presence of the HF alkylation catalyst to form isoparaffins which constitute a high octane gasoline boiling range product. The UOP and Phillips HF alkylation processes, which together provide substantially the entire alkylation capacity of the United States refining industry are described in Handbook of Petroleum Refining Processes, R. A. Meyers (Ed.), Chemical Process Technology Handbook Series, McGraw-Hill, New York 1986, ISBN 0-07-041763-6, to which reference is made for a description of these processes.

Two types of HF alkylation unit are in general use at the present time. In one type, the gravity flow type reactor, the hydrocarbon reactants meet the liquid hydrofluoric acid entering the bottom of the reactor from an acid cooler to which the acid flows from an acid settler after the alkylation reaction has taken place. The driving force for the circulation of the acid and the hydrocarbon reactants is the difference in density between the catalyst and the hydrocarbons at different points in the system aided by the jet action of the injection nozzles in the reactor. The acid settler permits a phase separation to take place between the denser acid phase and the lighter hydrocarbon phase. The acid phase is recycled to the acid cooler and then back to the reactor; the hydrocarbon phase including the alkylation product is fed to a fractionation section where the propane and unreacted isobutane are separated from the motor fuel alkylate fraction. The isobutane is recycled and propane is removed from the unit. A unit of this type is described in U.S. Pat. No. 3,716,343, to which reference is made for a description of the unit and its mode of operation.

The other principal type of unit currently in use is the pumped acid flow type in which the mixed hydrocarbon feed is introduced into the reactor through spargers along the vertical length of the reactor. From the reactor the catalyst and the hydrocarbons flow into an acid settler where a phase separation takes place in the same way as in the gravity flow unit, permitting product and catalyst recovery in the same manner as described above. Compared to the gravity flow reactor, the pumped circulation reactor uses a smaller inventory of acid because of the higher circulation speed of the catalyst in this type of unit and the smaller size of the piping utilised in the unit.

The petroleum refining industry has always recognised the potential for hazard created by HF alkylation units and has consistently ensured, by the superior mechanical and metallurgical specifications and operating practices utilised in the design, construction and operation of these units, that a high level of safety has been achieved; as a result, the HF alkylation process has enjoyed an almost unparalleled record of industrial safety. The industry has, however, been concerned that the intrinsic safety of these units should be enhanced to secure a higher level of potential operating safety and to guard against the consequences of an uncontrolled release of unit contents, however unlikely this may be. The potential magnitude of the risks inherent in operating an HF alkylation unit may be reduced by decreasing the inventory of acid in the unit and in one of its embodiments, the present invention enables the acid inventory to be reduced by a significant amount, even compared to the lower inventories used in the pumped circulation type of unit. In addition, the present invention enables the intrinsic safety factor of both the gravity flow and pumped circulation units to be increased by providing for the acid inventory to be stored at a remote, safe location away from the main body of the unit. The acid is stored in this location without risk of release during routine operation and during maintenance activity on the unit and can be evacuated to this safe location within a very short time if any uncontrolled release from the unit should occur.

SUMMARY OF THE INVENTION

The HF alkylation units which we have now devised have enhanced safety features which improve the intrinsic safety of the unit during normal operation and which, in addition, are capable of minimizing the effects of any uncontrolled release of unit contents. The features of the unit may be employed with units of existing types and may also be used in a unit of novel configuration which can be operated with a reduced inventory of acid.

According to the present invention, the HF alkylation unit includes an acid storage drum or receiver which is located at a safe, remote location away from the main body of the unit so that the amount of acid in the operational portion of the unit at any one time is minimized. The alkylation unit also includes an acid evacuation system connected to the acid receiver which enables the acid in the unit to be transferred from the reactor section of the unit during turn-around or maintenance activity or to be rapidly evacuated from the main body of the unit in the event of an emergency. In order to provide for rapid evacuation of the acid into the receiver, the receiver is provided with a venting system which allows the internal gas pressure of the receiver to be relieved through a relief gas scrubber in which the relief gases from the receiver can be scrubbed with an alkali to remove acidic components. Alternatively, the relief gases from the receiver may be vented from the receiver through the fractionation section to the normal acid relief neutraliser where the acid components of the gases may be removed in the normal way.

THE DRAWINGS

In the accompanying drawings:

FIG. 4A is a simplified vertical section of another form of acid settler for use in a reduced inventory unit of FIG. 3, and FIG. 4B is a simplified horizontal section of the acid settler of FIG. 4A.

DETAILED DESCRIPTION

Figure 1:
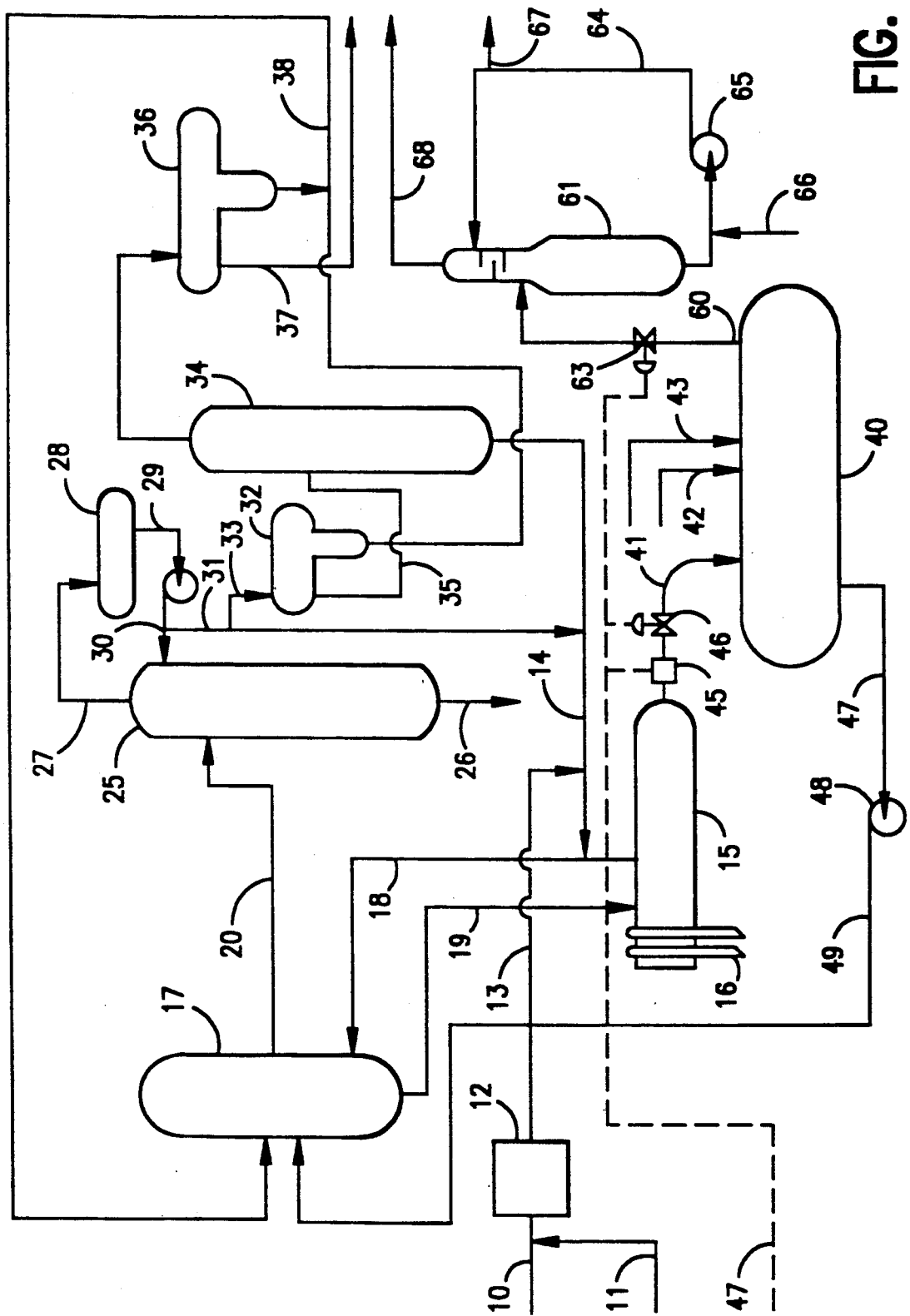
FIG. 1 is a simplified schematic of a gravity flow HF alkylation unit incorporating an acid evacuation system.

In the present HF alkylation unit, a large acid storage drum is provided which is capable of containing the entire acid inventory of the unit. It is important that the acid receiver should have a sufficient size to accept the entire contents of the unit which are likely to cause any hazard in the event of an uncontrolled release.

The acid receiver preferably takes the form of a large drum which is located remotely from the unit in an area which is sterile to maintenance activities so that routine plant maintenance will not impose any risk of hazard with the stored acid. It is preferred that the storage drum should be located a minimum of about 30 meters from process equipment containing HF. The drum may be located above or below grade but in either case, measures should be taken to maintain its structural integrity in the event of any explosion or fire in the unit itself or, for that matter, in other refinery units. The receiver should either be buried or surrounded by high blast walls extending above the top of the receiver to protect it from flying debris and fire. Transfer lines to the drum may be located above or below grade level although it should be realised that problems are inherent in either location: if the pipe is located in a trench below grade, there is always the possibility in a refinery that heavy hydrocarbon vapors will accumulate in the trench and create a risk of fire or explosion, even though the pipe itself is better protected from explosion hazards occurring elsewhere. Pipe inspection is also made more difficult. On the other hand, location of the transfer piping above grade improves access to the pipe for inspection and removes the risks associated with low level vapor accumulation. If desired, the transfer piping may be run between blast walls to provide protection from explosions taking place elsewhere.

The acid transfer line or lines which link the acid receiving or storage drum to the remainder of the unit are capable of evacuating the acid from the remainder of the unit in a very short time and is usually connected to the reactor section of the unit. Acid dump valves are located in the evacuation lines, to be actuated by a master evacuation controller in the event of an emergency. Actuation may be either manual or automatic. Once evacuation has been initiated, the evacuation valves remain open until the acid inventory has been drained into the receiver or, alternatively, densitometers located in the acid transfer line can be used to detect a difference in the density of the fluids flowing from the reaction section of the unit indicating a change from acid to hydrocarbon flow. Upon detecting this difference in density, the densitometers shut the dump valve, thus completing the evacuation of acid from the reactor system.

In order to ensure rapid transfer of the acid through the transfer lines to the receiver during an evacuation, the receiver is provide with a venting system which vents the gases from the receiver as the acid enters it. The vented gases pass into an acid relief neutraliser where the acid components are neutralised with caustic and other gases vented to the flare stack. In addition, the drum may be provided with sensors to prevent the drum overflowing to the acid relief neutraliser system e.g. displacement sensors, magnetic sensors, nuclear sensing devices.

The acid storage and evacuation system may be used during routine servicing on the unit and permits service operations to be carried out while the entire unit is free of any stored acid. Maintenance can therefore be conducted without any fear of accidentally damaging an on-site acid storage drum which could release acid to the atmosphere.

FIG. 1 of the drawings shows an acid storage and evacuation system employed in conjunction with a gravity flow type alkylation unit. This configuration is useful with existing units of this type. The olefin feed enters the unit through line 10 and is joined with isobutane make-up admitted through line 11. The combined feed passes through a dryer 12, usually a bauxite dryer, and enters line 13 through which it passes to the recycle line for isobutane 14. The alkylation mixture comprising hydrocarbons and acid circulates between acid cooler 15 fitted with cooling coils 16 and acid settler 17. Circulation takes place through riser 18 and recirculation line 19 connecting the settler to the cooler. The recycled isobutane together with fresh feed passes from line 14 into riser 18, where the reaction takes place and the mixture then passes into the acid settler. In the acid settler, a phase separation occurs with a supernatant hydrocarbon phase including alkylation product and a heavier, lower liquid phase containing the HF alkylation catalyst. The catalyst is continually removed from the lower portion of acid settler 17 through recirculation line 19 and passed to acid cooler 15 together with the hydrocarbons which accumulate in this phase. The hydrocarbon phase is withdrawn from the acid settler through line 20 and passed to isostripper 25 which functions as the main fractionator for the unit. Alkylate product is withdrawn as bottoms from the isostripper through line 26 and the isostripper overheads pass through line 27 to isostripper overhead accumulator 28 with recycle being provided through lines 29 and 30 to the top of the isostripper column. Isoparaffin recycle is returned through line 31 to recycle line 14 for mixing with fresh feed and circulating alkylation acid in riser 18. A portion of the reflux is withdrawn and passed to separator 32 through transfer line 33. The liquid hydrocarbon portion from separator 32 then passes to depropanizer 34 through line 35. The overhead from depropanizer tower 34 passes into separator 36 from which the liquid propane product is removed by line 37 and passed to the propane stripper (not shown). The separated liquids from separators 32 and 36, comprising significant quantities of acid are collected in line 38 and recycled to acid settler 17. A conventional treating section (not shown) may be provide to remove HF from the propane product e.g. a catalytic defluorinator and caustic potash treater to remove organic fluorides.

The acid storage and evacuation system comprises acid receiving drum 40 at a remote, safe location which is connected to cooler 15 by means of acid evacuation line 41. The contents of the drum are blanketed by nitrogen supplied through line 42. Fresh acid may be supplied to the alkylation unit by way of the acid receiving drum through line 43, for example, from a tank truck. A densitometer 45 is located in acid evacuation line 41 and is connected through suitable control circuitry to evacuation valve 46 which is also capable of being operated through control line 47 which is connected to the master controller of the acid evacuation system during normal operation. Acid may be supplied to the reactor portion of the alkylation unit by withdrawal from acid receiver drum 40 through line 47 connected to return pump 48 and acid return line 49 leading to acid settler 17. Thus, during normal operation of the unit, the bulk of the acid is stored away from the principal items of process equipment, thereby maintaining the required inventory of acid for proper unit operation but with a marked improvement in the intrinsic safety of the unit.

In the unlikely event of an emergency condition arising in the unit, an acid evacuation is initiated: acid evacuation valve 46 is opened by the master controller and the acid content of the alkylation unit is rapidly dumped into the acid receiver through evacuation line 41. To this end, line 41 has a large flow capacity sufficient on a design basis to dump the entire acid inventory of the unit in no more than about ten minutes and preferably not more than five minutes. The acid, being of greater density than the hydrocarbons in the unit, enters the evacuation line and receiving drum first with the hydrocarbons following. When the acid dump is complete, the evacuation valve 46 can be closed by manual or automatic control to seal the acid in the drum away from the main body of the unit. Automatic control may be provided by the densitometers which detect the interface between the denser acid and the less dense hydrocarbon passing in the transfer line. Densitometer 45 located in the acid transfer line detects the difference in densities and operates the associated control circuitry so that evacuation valve 46 is closed. At the same time, valve 63 in relief line 60 is closed by means of the control circuitry to seal the acid in receiving drum 40 in its remote, safe location so that any further release of acid from the alkylation unit is precluded. The acid is then maintained in a secure location regardless of untoward events elsewhere in the unit or the refinery as a whole.

In order to promote the rapid evacuation of the acid from the unit, the pressure in the receiving drum should be maintained at a lower value than that of the rest of the unit. Typically, the reactor will be at a pressure of about 50 to 100 psig (about 445 to 790 kPa abs), typically about 80 psig (about 650 kPa abs). The acid receiver is maintained at a lower pressure and usually, a pressure of from about 25 to 50 psig will be satisfactory. To this end, the nitrogen blanketing system is arranged to maintain the desired internal low pressure in the drum during normal operation. When the drum is being filled with acid or when the acid evacuation system is actuated, the nitrogen is shut off and the nitrogen and gases saturated with HF are vented through vent line 60 and associated vent gas scrubber 61. Vent gas line 60 enters the top of acid receiver 40 and provides a path for rapid escape of gas from the receiver when acid evacuation valve 46 is opened to permit the acid to be transferred rapidly into the receiver. The outlet of vent line 60 enters caustic scrubber 61 at the bottom end of scrubbing section 62 which is supplied with caustic scrubbing solution from a caustic scrubbing solution circuit. The scrubbing solution circuit comprises caustic circulation loop 64 with circulating pump 65 which circulates the scrubbing liquid in the scrubbing loop. The scrubbing solution comprises an alkaline solution which is capable of reacting with the acid component of the vent gases and is suitably an aqueous caustic soda solution, typically about 3-5% aqueous caustic. Fresh caustic makeup may be added through line 66 and spent caustic purge removed through purge line 67. When acid enters drum 40 either during evacuation, filling or normal operations, the gases are vented from the drum through line 60 and enter vent gas scrubber 61 in which the acid components react with the caustic scrub solution and are eventually removed through purge line 67. The nitrogen and hydrocarbon components less HF pass out of the scrubber through gas venting line 68 from which they may be led to a flare stack (not shown).

Figure 2:
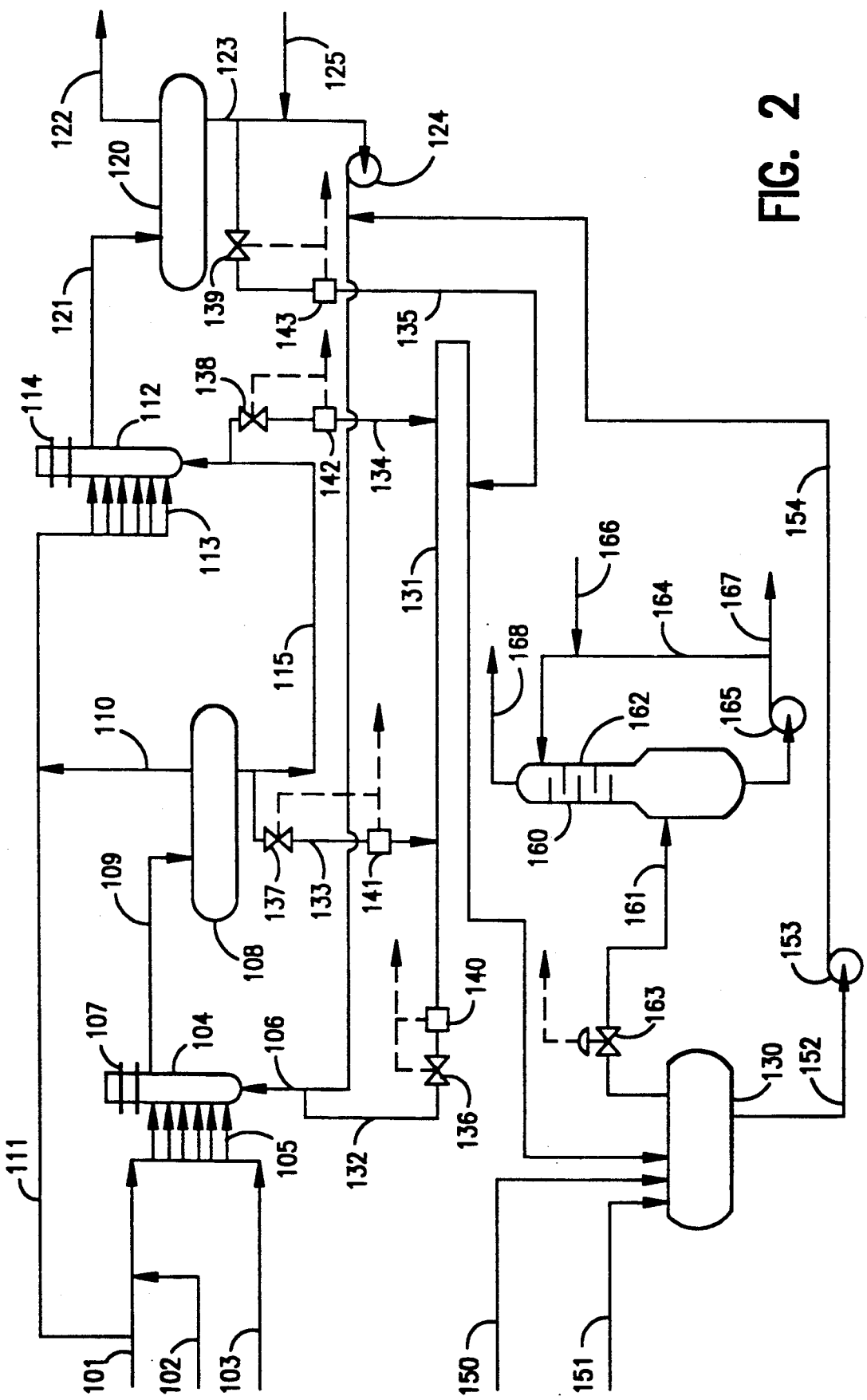
FIG. 2 is a simplified schematic of a two-reactor, pumped circulation HF alkylation unit incorporating an acid evacuation system.

FIG. 2 shows, in simplified form, a schematic of the reactor section of a pumped circulation HF alkylation unit of a conventional type using two alkylation reactors, but with a retrofitted acid storage and evacuation system. This unit configuration provides a high quality alkylate product by splitting the olefin feed to maintain a high isobutane:olefin ratio in the individual reactors. The fractionation section for recovery of hydrocarbon products and separation of acid from the products is omitted as it is of conventional configuration with isostripper and depropanizer and other associated equipment, suitably as illustrated in FIG. 1. The olefin feed is introduced through line 101 with isobutane makeup added through line 102. Isobutane recycle from the fractionation section enters through line 103. The hydrocarbon feed enters primary reactor 104 through a number of vertically spaced spargers 105 in order to ensure that good dispersion of the hydrocarbon takes place in the acid phase. Recycle acid enters the reactor at the bottom through line 106 and cooling is provided at the top of the reactor by cooling coils 107 in the conventional manner. The products from reactor 104 pass into primary acid settler 108 through line 109. In the acid settler a phase separation occurs with a supernatant hydrocarbon layer containing alkylate product, unreacted isobutane and other hydrocarbons and a lower, denser acid layer which collects in the lower portion of the acid settler. Hydrocarbons, including unreacted isobutane, pass out of the top of the settler through line 110 and are joined by additional olefin feed from line 111 and pass to secondary riser reactor 112 which is of similar form to the primary reactor 104 with spaced spargers for the hydrocarbon feed 113 and cooling coils 114. The acid phase is withdrawn from the primary acid settler through line 115 and enters the bottom of the secondary reactor to provide the catalyst for the alkylation reaction which takes place in the secondary reactor. Effluent from the secondary reactor passes to the secondary acid settler 120 through line 121 and again, phase separation takes place in the settler in the conventional manner. Hydrocarbon product from the secondary settler passes to the isostripper of the fractionation section through line 122 for recovery of alkylate product and other hydrocarbons as well as of acid which passes over with the hydrocarbons.

Acid from the lower layer in the acid settler is withdrawn through line 123 and returned through recycle pump 124 together with acid recycled from the fractionation section through line 125. The recycled acid passes back to the primary reactor 104 through line 106 from recycle pump 124. Thus, the acid is circulated in a closed loop cycle through the reactors and acid settlers in sequence with recycle from the second settler to the primary reactor together with acid which is recycled from the product recovery/fractionation section.

The acid storage and evacuation system in this unit comprises an acid receiver which is located away from the unit and protected from blast, as described above. The acid receiving drum is connected to the reactor section of the unit by means of acid main evacuation header 131 which is dimensioned so as to provide rapid evacuation of the acid from the unit into the drum when necessary. Again, a design basis for evacuation within 10 and preferably less than five minutes is desirable. Main evacuation header 131 is linked to individual items of process equipment by branch evacuation lines 132, 133, 134 and 135, each of which is provided with its own acid evacuation valve 136, 137, 138 and 139. Densitometers 140, 141, 142 and 143 are positioned in each branch evacuation line and are connected to their respective acid evacuation valves as shown and also to control circuitry (not shown) which opens the acid evacuation valves in response to a signal from the master evacuation control. When the acid evacuation valves are opened, the acid passes rapidly from the individual process units i.e. the settlers and their associated flow lines, through the branch evacuation lines and then, through main evacuation header 131 into acid receiving drum 130 until removal of the acid from the reactor section is complete, as monitored by the densitometers which then close the acid evacuation valves to seal the acid from the unit in the receiver. Inert gas blanketing for the receiver contents, suitably by nitrogen, is provided by blanket gas line 150 and additional acid may be supplied from a tank truck through acid inlet 151. Acid may be returned to the reaction section of the unit through acid return line 152 and return pump 153 leading through return line 154 to acid recycle line 106.

The locations where the acid evacuation lines enter the individual process equipment items are desirably determined by dynamic simulation modelling of the equipment so as to ensure that all the acid is removed from the equipment when an evacuation is initiated; the precise location will be determined by equipment and pipeline geometry in any given unit. The modelling will also determine, for any given unit, the optimum sequence for valve actuation to provide for the most rapid evacuation of the acid. Once the optimum sequence has been established, it can be programmed into the master evacuation controller for the unit so that when an evacuation is initiated, the acid removal takes place within the shortest time span. As mentioned above, the evacuation desirably takes place under the control of an evacuation controller, without any operator interface to ensure an optimal evacuation mode. The unit controller which is effective during normal operations may, however, be used to monitor the integrity of the evacuation system continually by checking controls e.g. checking to determine the presence of control signals and responses, and by stroking valves to ensure response to control signals and mechanical integrity.

In order to provide rapid venting for the acid receiver during an evacuation, the receiver is coupled to vent gas scrubber 160 through vent line 161, in the manner described above with respect to FIG. 1. Again, the vent gas scrubber is provided with a lower stripping section 162 and a caustic scrub loop 164 with scrub pump 165. Caustic makeup may be added through makeup line 166 and spent caustic purge removed through purge line 167. Receiver blanketing gas and light hydrocarbons are vented to flare stack through flare line 168. Closure valve 163 is connected to the evacuation controller to move to the closed position when the acid evacuation is complete to seal the acid into the storage drum, as described above.

Figure 3:
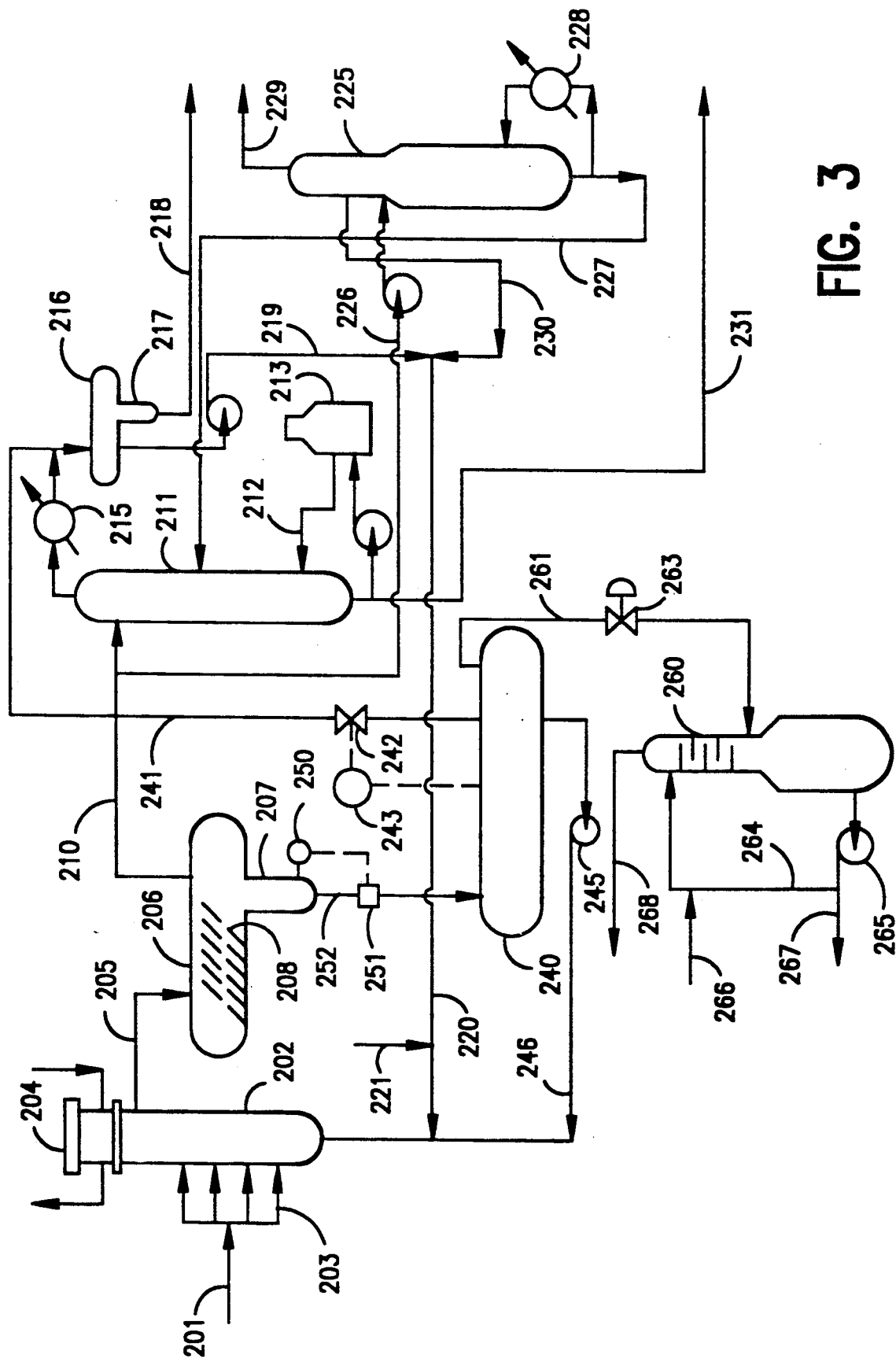
FIG. 3 is a simplified schematic of a single reactor, pumped circulation HF alkylation unit, using a riser reactor.

The acid storage and evacuation systems shown in FIGS. 1 and 2 are suitable, as noted, for incorporation in existing gravity flow and pumped circulation units, respectively, to improve the intrinsic operational safety of those units. The system shown in FIG. 3, by contrast, shows an acid storage and evacuation system employed in an HF alkylation unit of novel configuration which is designed to maximise the advantages of the system. The alkylation unit shown in FIG. 3 is designed to operate with a significantly reduced inventory of acid in order to effect a further improvement in the safety of the unit. This unit embodies the following design features:

1. A single stage reactor in which the isobutane recycle and acid enters the bottom of the reactor with olefin feed injected at several locations to produce a high isobutane/olefin ratio which is conducive to producing a high quality alkylate;
2. An acid settler fitted with coalescing baffles to enhance the separation of the acid from the hydrocarbon phase. The acid coalesces rapidly in the bottom of the settler and flows to a boot from which it flows to an acid receiver drum located off-site in a safe, remote location. The use of the boot on the acid settler enables the amount of acid in the settler to be reduced, and this effects a significant reduction in the acid inventory of the unit.
3. The acid receiver is maintained at a pressure which is lower than that of the acid settler to enable the acid to be transferred by pressure into the receiver. The pressure in the acid receiver is maintained by a balancing line to the operating pressure of the isostripper in the product recovery section. An acid transfer pump is used to transfer the acid from the receiver to the reactor.

Olefin feed is introduced into the unit through line 201 and enters reactor 202 through a number of separate, vertically spaced spargers, collectively indicated as 203, to achieve a high isobutaneparaffin/olefin ratio in the reactor in order to produce a high quality alkylate. The heat of reaction is removed by means of cooling coils 204 in the conventional manner with cooling provided by cold water. Reactor effluent passes through line 205 to acid settler 206 which is provided with an acid boot 207 and interior coalescing baffles 208. The coalescing baffles comprise flat, perforated or unperforated plates inclined at an angle to the horizontal inside the settler. A preferred form of the settler and its coalescing baffles is shown in FIG. 4 but the plates may, as shown in FIG. 3, be inclined at an angle to the horizontal, typically at angles from about 30° to 90°, preferably 45° to 90°, from the horizontal. The mixture of acid and hydrocarbon passing through the settler comes into contact with the plates to promote separation of the acid and hydrocarbon phases and the denser droplets of acid which separate from the acid/hydrocarbon mixture pass through the perforations in the coalescing plates to the bottom of the acid settler. The acid passes along the bottom of the settler vessel to the acid boot 207 and for this purpose, the plates may be provided with perforations along the junction with the bottom wall of the vessel to permit passage of the acid.

The improved separation in the settler minimizes residence time in the settler with a significant reduction in acid inventory resulting from the reduction in residence time. A further reduction in acid hold-up in the settler is provided by acid boot 207 which receives the denser acid phase and ensures that the acid is removed from the settler relatively free of hydrocarbons while minimizing the acid level in the settler. Thus, the level of acid in the main body of the settler is much lower than it would be in a conventional settler without the acid boot.

The hydrocarbon phase is removed from the settler through line 210 and passes into isostripper 211 which is maintained at an operating pressure of approximately 150 psig (about 1135 kPa abs). Reboil for the isostripper is provided by reboil loop 212 including circulation pump and heater 213. The overhead from the isostripper passes through heat exchanger 215 and then to isostripper overhead accumulator 216 which is maintained at an operating pressure of approximately 140 psig (about 1066 kPa abs). Acid, which collects in the overhead accumulator boot 217, is removed by line 218 and may be recycled to the reaction section of the unit in the conventional manner, typically to the bottom inlet of reactor 202. The isobutane-containing fraction from accumulator 216 passes through line 219 to isobutane recycle line 220 for return to the lower inlet of reactor 202 together with isobutane makeup introduced through line 221. The portion of the hydrocarbon effluent from acid settler 206 passes to depropanizer 225 by way of line 226. The bottoms fraction from depropanizer 225 is returned through line 227 to isostripper 211 with reboil for the depropanizer provided by heat exchanger loop 228. Propane product is removed from the depropanizer through propane product line 229. Isobutane from the depropanizer is sent to isobutane recycle line 220 by way of line 230. High quality, high octane alkylate product is removed from isostripper 211 as the bottoms fraction through line 231.

The acid storage and evacuation system comprises acid receiver drum 240 located in a remote, safe position, with staggered blast walls and protected from any potential fire or explosion, as described above. This drum is maintained at an operating pressure lower than that of the acid settler, the drum being typically about 150 psig (about 1135 kPa abs) with this pressure being maintained by balancing line 241 to the operating section of the isostripper. Pressure control valve 242 in balancing line 241 under control of pressure controller 243, which is also linked to acid receiver 240 is arranged to open pressure control valve 242 when pressure in the acid receiver exceeds the set value, for example, when the drum is being filled or during an acid evacuation. The pressure controller is also connected to the inert gas blanketing system to cut off gas supply when the pressure exceeds the preset value. When balancing valve 242 in line 241 is opened to relieve pressure build-up in receiver 240, the acid gases are vented through accumulator 216 to the normal relief neutraliser system associated with the unit (not shown). As a preferred alternative, however, the receiver is vented through a vent/scrubber system of the kind shown and described above with reference to FIGS. 1 and 2, with vent gas scrubber 260 connected to the receiver 240 by means of relief line 261 through closure valve 263. The scrubber is provided, as described above, with caustic circuit comprising circulation loop 264, circulation pump 265, caustic inlet 266 and spent caustic purge line 267. The scrubber is vented to a flare stack (not shown) through line 268. Closure valve 251 is controlled by the evacuation controller for sealing off the receiver when acid evacuation is complete. When the drum is vented in this way, the pressure balancing valve 242 is actuated during an acid evacuation to the closed position by the evacuation controller while the supply of blanketing gas cut off, to reduce the pressure in the drum to about 40 psig (about 380 kPa abs) to accelerate evacuation of the acid into the drum. Acid may be transferred from the receiver by way of transfer line 244, transfer pump 245 and return line 246 to the inlet of reactor 202. Acid receiver 240 may be provided with an inlet for fresh acid supplies and for inert gas blanketing, as described above.

The reduced acid inventory in the unit of FIG. 3 can be quickly dumped into the acid receiver if a leak in the reactor system occurs. The acid dump may be activated by a single control function e.g. single emergency push button, which initiates the following emergency cycle under the control of a master evacuation cycle controller which controls the acid evacuation independently of the normal operating controller:

1. The acid return pump 245 is shut off and blocked by a shutdown valve (not shown) in the acid return line.
2. Olefin feed is cut off and isobutane recycle is continued to purge the acid content of the reactor and to maintain pressure in the settler.
3. Densitometer 250 on acid boot 207 takes over control of valve 251 to permit the acid to be dumped from the settler boot 207 through dump valve 251 into acid transfer line 252 and then to the receiver 240. When densitometer 250 detects a difference in the density of the flowing fluids from acid to hydrocarbon flow, the densitometer shuts dump valve 251, thus completing evacuation of acid from the reactor section of the unit.

Upon return to normal conditions, unit operation can be restored by returning acid flow through acid return line to the reactor with hydrocarbon feed being restored through the appropriate inlets.

The preferred configuration of the acid settler is shown in FIGS. 4A and 4B. The settler comprises a horizontal, cylindrical vessel 300 fitted with inlet 301 for receiving the acid/hydrocarbon mixture from the reactor. The inlet has a vertical extension 302 on the interior side of the tank with a liquid port 303 facing the end wall of the vessel to minimise jetting of the incoming fluids into the settling area. A number of coalescing baffles 304 (one indicated) are disposed along the length of the vessel to promote phase separation between the acid and hydrocarbon phases. The baffles depend from the top of the vessel and, in plan view, are arranged to provide a sinuous course for the liquids as they pass from inlet 301 to the outlets at the opposite end. As the mixture of acid and hydrocarbons comes into contact with the baffles the drops of acid entrained in the hydrocarbon phase coalesce upon contact with the baffles and fall to the bottom of the vessel to form a lower acid layer 305 and a supernatant hydrocarbon layer 306. The hydrocarbons pass along the settler towards hydrocarbon outlet 307 and then pass to the fractionation section of the unit. The coalesced layer of acid passes along the bottom of the settler towards acid collection boot 308 where the acid collects before passing to the acid receiver, as described above. The provision of the baffles in the settler increases the surface area with which the incoming mixture comes into contact and this, in turn increases the rate of separation of the two phases. This enables the residence time in the settler to be decreased with a consequent favorable decrease in acid hold-up in the settler.

A notable feature of this type of unit is the reduction in the acid inventory which is achieved by the measures set out above. Typically, the acid inventory in the unit can be reduced to about 12,000 gallons for a unit producing 18,000 bpsd of alkylate product, as compared to an inventory of about 70,000 gallons for a gravity flow unit of the same size. This reduction is achieved by the use of the pumped acid system in conjunction with the acid settler fitted with coalescing baffles and acid boot for improved, short residence type separation of the hydrocarbon and acid phases in the settler. In addition, the location of the acid receiver off-site at a remote, safe location with suitable measures provided to protect the acid transfer lines ensures that the acid is kept under conditions of the utmost security regardless of what may happen in the alkylation unit itself or elsewhere in the refinery. The unit provides improved safety both during normal operation of the unit and during unit turnaround when the entire reaction and fractionation portions of the unit will be free of any acid being stored. Maintenance may therefore be conducted without any fear of accidentally damaging an on-site acid storage drum which could release acid to the atmosphere. The unit is therefore capable of achieving the advantages of the HF alkylation process in a while achieving improved intrinsic safety factors, both during normal operation as well as in the unlikely event of an accident occurring in the unit or elsewhere in the refinery.

We claim:

1. In an HF alkylation unit comprising a reactor section comprising an alkylation reactor in which isoparaffins are alkylated with olefins in the presence of an HF alkylation catalyst, means for supplying isoparaffin and olefin to the alkylation reactor, means for supplying HF alkylation catalyst to the reactor, means for separating hydrocarbons from HF in the effluent from the reactor and a fractionation section for separating alkylate product from the separated hydrocarbons, the improvement which comprises an acid evacuation system comprising an acid receiver for receiving the acid from the unit, at least one acid evacuation conduit connecting the acid receiver to the reactor section of the unit, an acid evacuation valve in each said acid evacuation conduit which is actuatable to an open position to evacuate acid from the reactor section of the unit to the acid receiver, means for maintaining the acid receiver at a pressure below that of the reactor section of the alkylation unit such that when the acid evacuation valve is actuated to the open position, acid is evacuated from the reaction portion of the unit to the acid receiver under positive pressure from the reactor section of the unit.

2. An HF alkylation unit according to claim 1 which includes means for maintaining the pressure in the acid receiver at a value below that of the reactor.

3. An HF alkylation unit according to claim 1 which includes an acid settler and means for maintaining the pressure in the acid receiver at a level below that of the acid settler.

4. An HF alkylation unit according to claim 2 in which the means for maintaining the pressure in the acid receiver comprises a pressure balancing line connecting the acid receiver to the fractionation system of the unit.

5. An HF alkylation unit according to claim 4 in which the fractionation system includes an isostripper for separating isoparaffins from the hydrocarbon effluent of the acid settler and in which the pressure balancing line connects the acid receiver to an overhead line of the isostripper.

6. An HF alkylation unit according to claim 4 in which the fractionation section includes an isostripper for separating isoparaffins from the hydrocarbon effluent of the acid settler; the isostripper having an overhead accumulator, connected to the isostripper overhead line, for separating liquid acid from the isostripper overhead and to which the pressure balancing line from the acid receiver is connected.

7. An HF alkylation unit according to claim 1 which includes a main acid evacuation conduit and a plurality of branch acid evacuation conduits connected to the main conduit, each branch conduit having an acid evacuation valve connected to a densitometer in the branch conduit for detecting the flow of hydrocarbons in the branch conduit and actuating the valve to a closed position upon the detection of hydrocarbon flow in the conduit.

8. An HF alkylation unit according to claim 1 which includes an acid settler in the reactor section having coalescing baffles inclined at an angle from about 30° to about 90° to the horizontal inside the settler to promote phase separation of hydrocarbons from a denser acid phase in the settler.

9. An HF alkylation unit according to claim 3 in which the acid settler includes a main body portion in which separation of the acid and hydrocarbon phases takes place and an acid boot section depending from the main body portion for receiving acid from the main body portion.

10. An HF alkylation unit according to claim 9 in which the bottom of the acid boot is connected by means of an acid evacuation conduit to the acid receiver, the conduit having an acid evacuation valve which is actuatable to an open position to permit acid to flow from the acid boot to the acid receiver.

11. An HF alkylation unit according to claim 10 which includes a densitometer for detecting a phase interface in the acid boot between hydrocarbons and acid and actuating the acid evacuation valve to a closed position upon the detection of the phase interface.

* * * * *